United States Patent [19]

Chin et al.

[11] Patent Number: 5,431,173
[45] Date of Patent: Jul. 11, 1995

[54] METHOD AND APPARATUS FOR BODY STRUCTURE MANIPULATION AND DISSECTION

[75] Inventors: Albert K. Chin, Palo Alto; Frederic H. Moll, San Francisco; Gail Stevens, Palo Alto; Robert D. Warner, Cupertino, all of Calif.

[73] Assignee: Origin Medsystems, Inc., San Carlos, Calif.

[21] Appl. No.: 890,941

[22] Filed: May 29, 1992

Related U.S. Application Data

[63] Continuation-in-part of Ser. No. 762,318, Sep. 19, 1991, Pat. No. 5,370,134, which is a continuation-in-part of Ser. No. 706,781, May 29, 1991, abandoned.

[51] Int. Cl.$^6$ .................... A61B 19/00; A61M 29/00
[52] U.S. Cl. .................... 128/898; 606/191; 606/167; 604/104
[58] Field of Search .................... 604/96–102, 604/104, 164, 170; 606/49, 108, 127, 167, 169, 171, 172, 180, 185, 190, 191, 192, 198; 128/898

[56] References Cited

U.S. PATENT DOCUMENTS

| | | |
|---|---|---|
| 1,060,350 | 4/1913 | Miller . |
| 1,275,520 | 8/1918 | Bell . |
| 1,618,261 | 2/1927 | Arbogast . |
| 1,947,649 | 2/1934 | Kadavy . |
| 2,663,020 | 12/1953 | Cushman . |
| 2,841,148 | 7/1958 | Kadavy . |
| 3,039,486 | 7/1962 | Price . |
| 3,168,092 | 2/1965 | Silverman . |
| 3,460,539 | 8/1969 | Anhalt, Sr. . |
| 3,626,949 | 12/1971 | Shute . |
| 3,717,151 | 2/1973 | Collett . |
| 3,774,596 | 11/1973 | Cook . |
| 3,782,370 | 1/1974 | McDonald . |
| 3,831,587 | 8/1974 | Boyd . |
| 3,863,639 | 2/1975 | Kleaveland . |
| 3,961,632 | 6/1976 | Moossun . |
| 4,052,980 | 10/1977 | Grams . |
| 4,077,412 | 3/1978 | Moossun . |
| 4,083,369 | 4/1978 | Sinnveich . |
| 4,137,906 | 2/1979 | Akiyama et al. . |
| 4,240,433 | 12/1980 | Bordow . |
| 4,254,762 | 3/1981 | Yoon . |
| 4,271,839 | 6/1981 | Fogarty et al. ............... 606/194 |
| 4,291,687 | 9/1981 | Sinnreich . |

(List continued on next page.)

FOREIGN PATENT DOCUMENTS

| | | |
|---|---|---|
| 516114 | 5/1981 | Australia . |
| 0010650 | 5/1980 | European Pat. Off. . |
| 0246086 | 11/1987 | European Pat. Off. . |
| 0251976 | 1/1988 | European Pat. Off. . |
| 0275230 | 7/1988 | European Pat. Off. . |

(List continued on next page.)

OTHER PUBLICATIONS

Ed. G. Berci, *Endoscopy*, Appleton–Century–Crofts, 1976, pp. 382–385 and 412.

(List continued on next page.)

*Primary Examiner*—Ren Yan
*Attorney, Agent, or Firm*—Heller, Ehrman, White & McAuliffe

[57] ABSTRACT

Hollow body structures may be manipulated and dissected from surrounding tissue using a manipulator device and a dissection device. The manipulator includes a rigid shaft having an inflatable balloon at its distal end. By inserting the balloon through a wall of the body structure and inflating the balloon, the body structure can be manipulated using the shaft to expose a dissection plane in an optimum manner. The dissection device is used to separate the body structure from its surrounding tissue. The separator device includes a separator head which is a cylindrical body having a plurality of axial channels therein. The dissector head is rotated or oscillated at a high frequency and acts to separate the body structure from the surrounding tissue with minimum damage.

31 Claims, 11 Drawing Sheets

U.S. PATENT DOCUMENTS

| | | | |
|---|---|---|---|
| 4,318,410 | 3/1982 | Chin . | |
| 4,357,940 | 11/1982 | Muller . | |
| 4,430,076 | 2/1984 | Harris . | |
| 4,447,227 | 5/1984 | Kotsanis . | |
| 4,459,978 | 7/1984 | Kotsanis . | |
| 4,493,711 | 1/1985 | Chin . | |
| 4,535,773 | 8/1985 | Yoon . | |
| 4,598,699 | 7/1986 | Garren . | |
| 4,601,710 | 7/1986 | Moll . | |
| 4,654,030 | 3/1987 | Moll . | |
| 4,705,040 | 11/1987 | Mueller . | |
| 4,709,697 | 12/1987 | Muller . | |
| 4,744,363 | 5/1988 | Hasson . | |
| 4,765,331 | 8/1988 | Petruzzi . | |
| 4,775,371 | 10/1988 | Mueller, Jr. . | |
| 4,779,611 | 10/1988 | Grooters . | |
| 4,863,440 | 9/1989 | Chin . | |
| 4,919,152 | 4/1990 | Ger . | |
| 4,944,443 | 7/1990 | Oddsen . | |
| 4,966,583 | 10/1990 | Debbas | 604/98 |
| 4,984,564 | 1/1991 | Yuen . | |
| 5,002,557 | 3/1991 | Hasson . | |
| 5,007,898 | 4/1991 | Rosenbluth . | |
| 5,062,847 | 11/1991 | Barnes . | |
| 5,082,005 | 1/1992 | Kaldany . | |
| 5,083,576 | 1/1992 | Ruiz-Razura . | |
| 5,100,426 | 3/1992 | Nixon . | |
| 5,122,122 | 6/1992 | Allgood . | |
| 5,159,925 | 11/1992 | Neuwirth et al. | 128/401 |
| 5,176,128 | 1/1993 | Andrese . | |
| 5,176,697 | 1/1993 | Hasson . | |
| 5,183,463 | 2/1993 | Debbas | 604/96 |
| 5,183,464 | 2/1993 | Dubrul et al. | 604/96 |
| 5,195,505 | 3/1993 | Josefsen . | |
| 5,195,959 | 3/1993 | Smith | 606/41 |
| 5,197,948 | 3/1993 | Ghodsian | 606/96 |
| 5,197,971 | 3/1993 | Bonutti | 604/96 |
| 5,201,752 | 4/1993 | Brown et al. | 606/190 |

FOREIGN PATENT DOCUMENTS

| | | |
|---|---|---|
| 2474304 | 7/1981 | France . |
| 2646088 | 10/1990 | France . |
| 1516411 | 7/1969 | Germany . |
| A 2847633 | 5/1979 | Germany . |
| 8516286 | 9/1985 | Germany . |
| 2071502 | 9/1981 | United Kingdom . |
| 736949 | 5/1980 | U.S.S.R. . |
| 797668 | 1/1981 | U.S.S.R. . |
| 1367947 | 1/1988 | U.S.S.R. . |
| 1577769 | 7/1990 | U.S.S.R. . |
| WOA9102493 | 3/1991 | WIPO . |
| WOA91/143-92 | 10/1991 | WIPO . |
| WO91/14392 | 10/1991 | WIPO . |

OTHER PUBLICATIONS

Unknown—Laparoscopy for Sterilization, Section 1, A Chronology of Laparoscopy.

"New Surgical Procedures for Indirect Hernias"—Product leaflet for Herniastat TM disposable automatic surgical stapling device published by Innovative Devices, Inc., date unknown.

"A tiny TV Camera is fast transforming Gallbladder Surgery," *Wall Street Journal*, Dec. 10, 1990, P. A1, continued on p. A5.

*A Comprehensive Guide to Purchasing* (Hospital Supplies), V. Mueller & Co. Chicago, 1956, P. 829.

Nagai, "A New Method of Laparoscopic cholecystectomy: An Abdominal Wall Lifting Technique without Pneumoperitoneum," *Surgical Laparoscopy and Endoscopy*, vol. 1, No. 2, 1991, P. 126.

Gazayerli, "The Gazayerli Endoscopic Retractor Modell," *Surgical Laparoscopy and Endoscopy*, vol. 1, No. 2, 1991, p. 98–100.

Jako, "Preliminary Report: Endoscopic Laser Microsurgical Removal of Human Gallbladder," *J. Laparoendoscopic Surgery*, vol. 1, No. 4, 1991.

Keen, "Operative Surgery & Management," P. 334–335, 2nd, ed., Wright, Bristol, 1987.

Rintoul (ed.). "Farquharson's Textbook of Operative Surgery," P. 286–289, (7th ed., Churchill Livingstone, New York, 1986).

Pietrafitta, *Gastrointensinal Endoscopy*, 37:338–343, 1991.

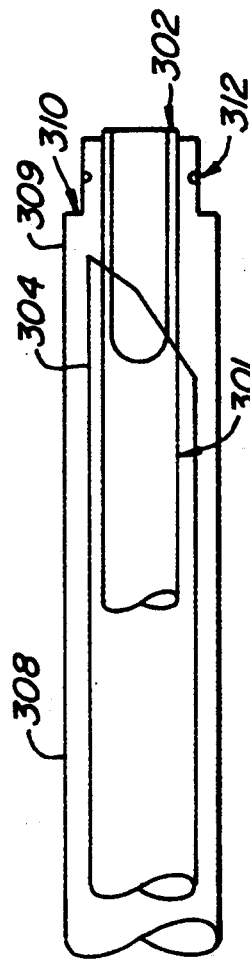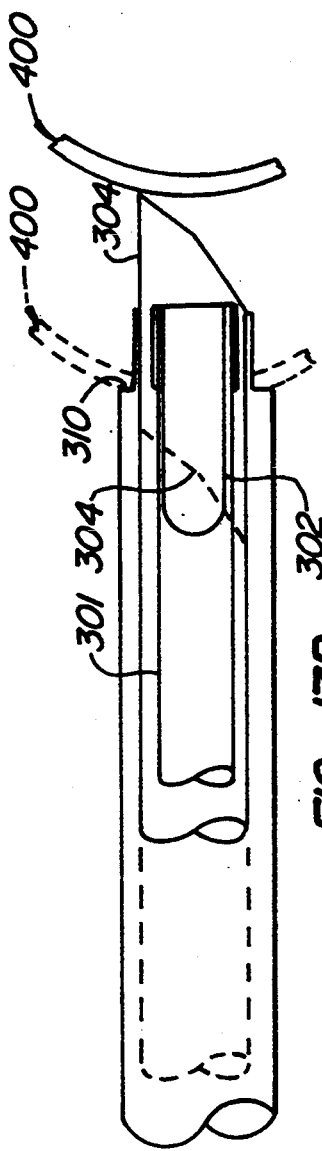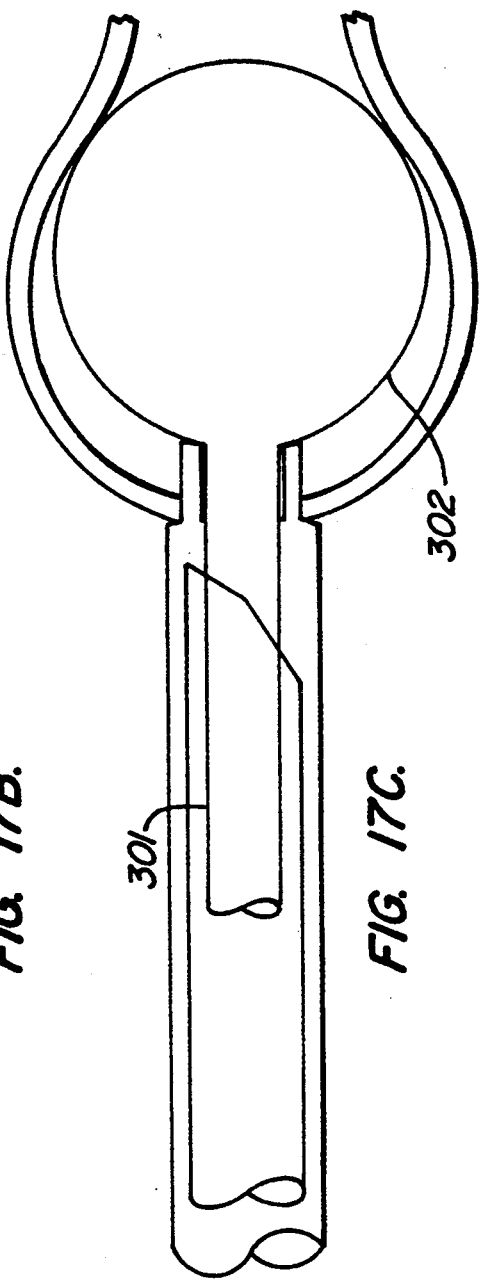

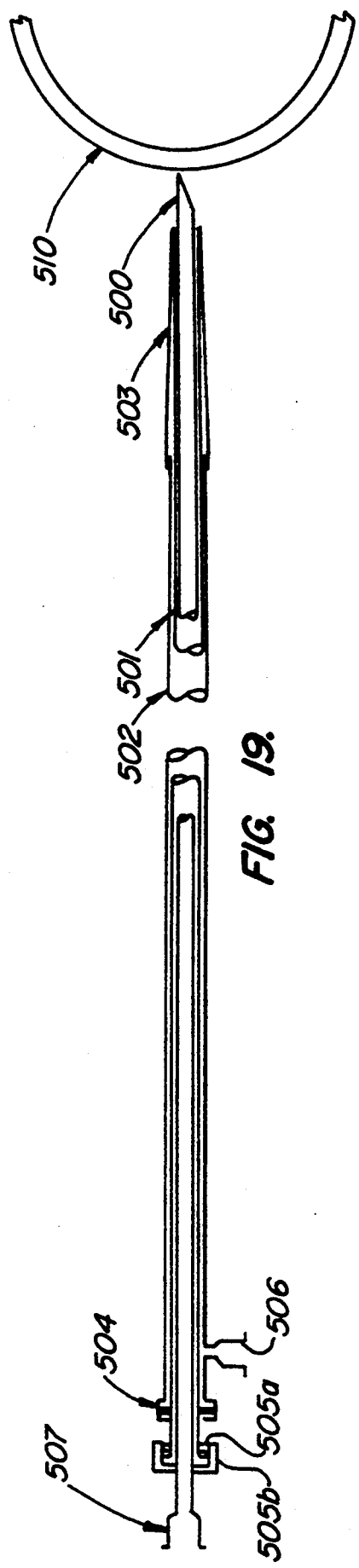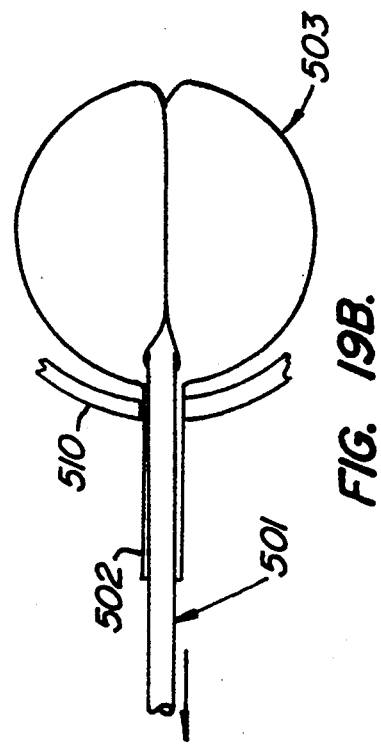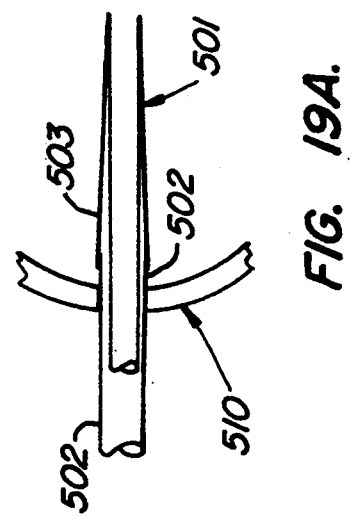

METHOD AND APPARATUS FOR BODY STRUCTURE MANIPULATION AND DISSECTION

This application is a continuation-in-part of application Ser. No. 07/762,318, now U.S. Pat. No. 5,370,134, filed September 19, 1991, which is a continuation-in-part of Ser. No. 07/706,781, filed on May 29, 1991, now abandoned, the full disclosures of which are incorporated herein by reference.

BACKGROUND OF THE INVENTION

1. Field of the Invention

The present invention relates generally to the structure and use of surgical instruments, and more particularly to a method and apparatus for manipulating and dissecting body structures during surgical procedures.

Minimally invasive surgical (MIS) techniques, such laparoscopic, endoscopic, and arthroscopic surgery, are generally performed through small incisions using specialized instruments to accomplish the desired surgical procedure. Usually, the instruments are introduced through a narrow-diameter tube, such as a trocar sleeve, while the physician observes manipulation of the instruments through specialized imaging equipment, such as laparoscopes, endoscopes, and arthroscopes. Such MIS techniques offer significant advantages over conventional "open" surgical procedures. In particular, the MIS techniques are usually less traumatic, require a shorter recovery time, and are less costly than corresponding conventional surgical procedures.

Of particular interest to the present invention are laparoscopic cholecystectomy procedures where the gallbladder is surgically severed (commonly referred to as dissected) and withdrawn through a small trocar sleeve, typically having a diameter of about 10 mm. In order to manipulate the gallbladder, several grasping forceps are introduced through additional trocar sheaths, and the position of the gallbladder is constantly changed in order to expose the interface between the gallbladder and surrounding tissue, particularly the liver, to permit dissection. The actual dissection has usually been performed using forceps, hooks, and/or a small gauze pledget to tear and tease the gallbladder from the surrounding tissue along the dissection plane.

While laparoscopic cholecystectomy procedures have been very successful and have become increasingly common, the need to simultaneously handle multiple graspers as well as a dissection instrument places great demands on the physician and usually requires coordination with one or more surgical assistants. The difficulty in performing the procedure is exacerbated by the slickness of the gallbladder surface, and overly vigorous attempts to capture the gallbladder can result in perforation, bile spillage, and gallbladder collapse. A collapsed gallbladder is even more difficult to dissect from the surrounding tissue than an intact gallbladder.

For these reasons, it would be desirable to provide improved methods and apparatus for manipulating and dissecting gallbladders during laparoscopic cholecystectomy procedures. It would be particularly desirable if such methods and apparatus were suitable for performing manipulation and dissection of other body structures during other surgical procedures. The method and apparatus should provide for controlled movement and manipulation of the body structure, preferably using a single instrument that can be manipulated by the physician with one hand. In the case of the gallbladder, the instrument should minimize the likelihood of bile spillage and should assure that the gallbladder remains expanded, preferably distended, to better present the dissection plane during the procedure. The method and apparatus should further provide for improved dissection techniques with reduced bleeding and tearing of the gallbladder, optionally providing for electrocautery capabilities.

2. Description of the Background Art

U.S. Pat. No. 4,430,076, describes a device for manipulating the uterus during examination procedures. The device is a handle having a balloon at its end, where the balloon is introduced through the cervix, inflated, and the handle is used to manipulate the uterus for examination purposes. Pietrafitta et al. (1991) Gastrointestinal Endoscopy 37:338–343, discloses the use of a dilating balloon to distend the pylorus during laparoscopic pyloromyotomy.

SUMMARY OF THE INVENTION

According to the present invention, improved methods and apparatus are provided for manipulating and dissecting body structures during surgical procedures, such as the gallbladder during laparoscopic cholecystectomy procedures. The methods comprise introducing an expandable member disposed on the distal end of a rigid shaft into the interior of the body structure, usually through a penetration in the body structure wall. The expandable member is then expanded to occupy at least a major portion of the interior volume, and the body structure can then be manipulated using the proximal end of the rigid shaft which remains available to the treating physician outside of the patient's body. Using the shaft, the physician can manipulate the hollow body structure with a single hand and can dissect the structure from surrounding tissue using a dissection instrument with the other hand. Positioning of the body structure is much easier and can be more precisely controlled than was possible using multiple grasping instruments. Moreover, the need to employ surgical assistants for positioning the body structure is reduced or eliminated entirely. Additionally, internal expansion of the body organ permits distention (over expansion) to better present the dissection plane during the dissection procedure.

In a first preferred aspect of the present invention, the expandable member and shaft are introduced through a penetration formed by advancing a sharp tip at the distal end of the shaft through a wall or the body structure. The expandable member is disposed proximally of the sharp tip and enters the interior of the body structure by continuing to advance the shaft in the direction of penetration. Usually, the sharp tip will be protected immediately after the initial penetration in order to prevent undesired perforations or other injury to the body structure. Protection can be achieved by either retraction or shielding or the tip, as described in more detail in connection with the apparatus hereinafter. In some cases, however, the dissection method of the present invention will rely on introducing the shaft and expandable member through a natural body orifice and will not require penetration of a wall of the body structure.

In a second preferred aspect of the method of the present invention, the gallbladder will be drained of bile prior to expansion of the expandable member, and the wall penetration will be aspirated during the remainder of the procedure to prevent bile leakage. Such drainage and aspiration are preferably effected by using particular drainage and aspiration lumens within the apparatus of the present invention, as described in more detail hereinbelow.

Apparatus according to the present invention include a device for manipulating the hollow body structure, where the device comprises a rigid shaft having a proximal end and a distal end, and an expandable member disposed near the distal end of the shaft. The expandable member is usually an elastic balloon which can expand and conform to the interior of the hollow body structure, although other expansion means such as expandable cages and coils would also be suitable.

A first embodiment of the manipulating device will include both a sharp tip and a blunt tip disposed near the distal end of the rigid shaft. Means will be provided for axially translating the sharp tip relative to the blunt tip, so that the sharp tip can be advanced and exposed during the initial stages of the procedure when the wall of the body structure is to be penetrated. After the device has entered the interior of the body structure, the blunt tip can then be advanced relative to the sharp tip (or the sharp tip retracted relative to the blunt tip) to protect the sharp tip and reduce the risk of unintended perforations and other injuries to the body structure.

In a second embodiment, the manipulation device of the present invention will include means for draining bile from the interior of the gallbladder and for aspirating leakage which may occur around the site of device penetration into the gallbladder. The drainage means will usually comprise a lumen within the rigid shaft which can be connected at its proximal end to a suitable vacuum (aspiration) source. The aspiration means will usually comprise an outer tube or sleeve which is coaxially disposed over the rigid shaft. The aspiration sleeve will usually include a resilient tip which can seal about the site of penetration, and the proximal end of the sleeve will be attached to a suitable vacuum (aspiration) source. Numerous specific designs for providing the desired drainage end aspiration capabilities may be provided.

Apparatus according to the present invention also include a dissection device comprising a shaft having a specialized dissection head. The dissection head comprises a cylindrical body having a plurality of axially oriented channels circumferentially spaced-apart thereabout. Means are provided for driving the dissection head, either by rotation or oscillation, at a relatively high rate, typically in the range from about 2000 rpm or Hz to 20,000 rpm or Hz. Preferably, the dissection head will have a length in the range from about 2 mm to 20 mm, preferably from about 5 mm to 15 mm, a diameter in the range from 1 mm to 10 mm, preferably from about 1.5 mm to about 4 mm, and from about 4 to 10 axial channels disposed thereabout. Such a dissection device has been found to effectively separate body structures, such as the gallbladder from surrounding tissues, with a minimum of tearing and bleeding in either the body structure or the tissue.

Methods according to the present invention will further comprise use of the dissection device, either in combination with the manipulator device or separately from the manipulation device.

BRIEF DESCRIPTION OF THE DRAWINGS

FIGS. 15, 1, 18, 18A and 19 illustrate preferred embodiments of the manipulating device of the invention.

FIGS. 17A, B and C illustrate the use of the devices in FIGS. 15 and 16.

FIGS. 19A and B illustrate the use of the device in FIG. 19.

DESCRIPTION OF THE SPECIFIC EMBODIMENTS

Figure 1:
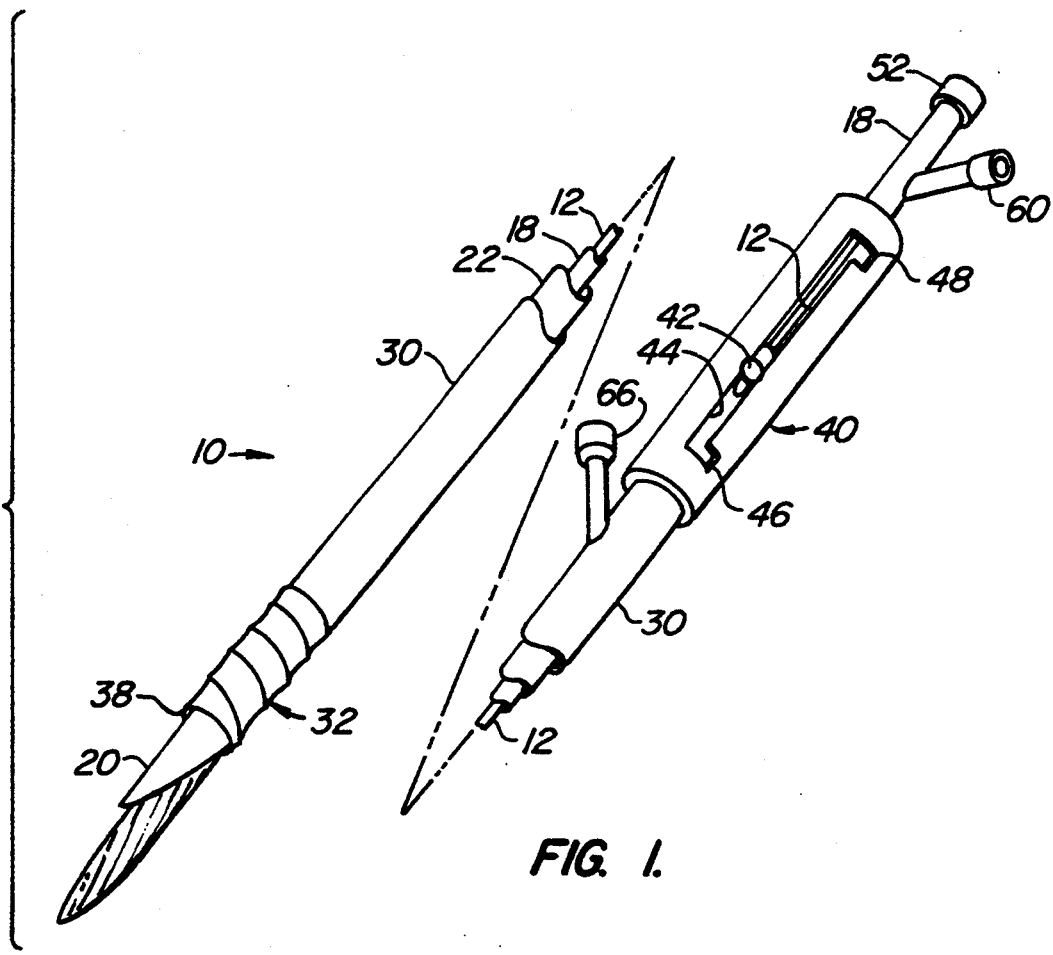
FIG. 1 is a perspective view of a body structure manipulator device constructed in accordance with the principles of the present invention.

The method and apparatus of the present invention are useful for manipulating and dissecting a variety of body structures in surgical procedures, particularly minimally invasive surgical (MIS) procedures where the apparatus are introduced through narrow diameter trocar sleeves and manipulated under the control of imaging equipment, as described generally above. While the methods and apparatus are particularly useful for removing the gallbladder during laparoscopic cholecystectomy procedures, as will be described in detail below, they will also be useful for treating other body organs and structures during other surgical procedures, both MIS and conventional open surgical procedures. For example, the methods and apparatus of the present invention will be useful for the partial or total removal of the stomach in gastrectomy procedures; manipulation of the intestines during bowel resection and other procedures; manipulation of the uterus in hysterectomy procedures; manipulation of a segment of the lung in lung resections; manipulation of pericardial cavity in cardiac diagnostic and therapeutic procedures including endocardial mapping, ablation, and defibrillation electrode placement; and the like. This list of body structures and procedures is not meant to be exhaustive, and the methods and apparatus of the present invention may find a variety of additional uses.

The methods of the present invention rely on introducing an expandable member to the interior volume of a hollow body structure, usually through a penetration formed in the wall of the structure. Direct entry of the expandable member through the structure wall is usually preferable to entry through a natural orifice, either because no natural orifice is available (e.g., in the case of the gallbladder) or because the entry path through the orifice is so long or tortuous that it impedes subsequent manipulation of the body structure (e.g., introduction through the esophagus into the stomach and through the vagina and cervix into the uterus). In some cases, however, it may be feasible to introduce the expandable member through a natural body orifice in such a way that permits subsequent manipulation, although it will generally be less preferred.

It will be appreciated that in certain methods of utilizing the present invention, such as during the removal of a gallbladder, a lifting device such as a compression balloon will be first inserted into the abdominal cavity to displace the liver and gallbladder for access. By providing such access to the gallbladder, it may be laparoscopically gripped the externally of the lifting balloon in the abdominal cavity and then dissected. Various mechanical extraction schemes of the abdominal cavity to allow intraperitoneal placement via small incisions or puncture sites, may be accomplished by means of either externally disposed posts or mechanical arms, or by means of inflatable bags or balloons which are expanded within the abdomen. A small opening is formed in the abdominal wall and lifting device is inserted into the abdomen through the opening in a contracted state. Once within in the abdomen, the device is extended to engage an extensive area of the abdominal wall and the wall is lifted with the device. The lifting device facilitates certain operations utilizing the present invention on such organs such as the gallbladder.

The expandable member will be located at the distal end of a rigid shaft which permits manipulation of the body structure from its proximal end. By "rigid" it is meant that the shaft will have minimum flexibility so that manipulation at the proximal end will be transmitted with minimum deflection to the distal end (where the expandable member is disposed within the body structure). Usually, the rigid shaft will be composed of metal, such as surgical stainless steel, although rigid plastic shafts may also find use.

In a preferred embodiment of the present invention, a sharp tip will be provided at or near the distal end of the rigid shaft. The sharp tip may be formed as a part of or integrally with the rigid shaft, or may be formed on a separate tubular or other member which is associated with the rigid shaft. The sharp tip is provided to effect the initial penetration through the body structure wall, and the method of the present invention will usually provide for protection or shielding of the sharp tip after the penetration has bean made. Specific approaches for protecting the sharp tip will be described in more detail in connection with the apparatus hereinafter.

Once inside the hollow body structure, the expandable member will be expanded to fill at least a major portion of the interior volume. It will be appreciated that the degree of contact between the expandable member and the interior wall of the body structure will in large part determine the degree of control which can be exercised over the structure. Thus, by expanding the expandable member to occupy substantially the entire interior volume of the hollow body structure, a great degree of control can be obtained. In many cases, it will be desirable to expand the expandable member sufficiently to distend the body structure (i.e., stretch the structure outward in all directions) so that the structure is firmly held by the expandable member on the rigid shaft. Such distension allows highly controlled manipulation and also serves to expose the dissecting plane by stretching the boundary interface between the structure and the surrounding tissue. In this way, the body structure can be pushed, pulled, turned, and otherwise manipulated during the dissection or other procedure.

The methods of the present invention further provide for removal and containment of the contents of the body structure, minimizing the risk that the contents will be accidentally spilled or leaked during the procedure. In conventional cholecystectomy and other procedures, the contents of the body structure are normally not removed since they maintain the shape of the structure and facilitate dissection. With the present invention, however, it is possible to remove the contents and thereafter expand the body structure from the interior to maintain the desired shape and facilitate dissection. Conveniently, removal of the contents of the body structure can be achieved by drainage through the shaft while containment around the site of penetration is achieved using a separate sealing member.

Referring now to FIGS. 1–4, a first embodiment of a manipulation device 10 constructed in accordance with the principles of the present invention will be described. The manipulation device 10 comprises a rigid shaft 12 having an expandable member 14 located at its distal end. As illustrated, the expandable member 14 is an inflatable balloon formed from an elastic material, such as silicone rubber, latex rubber, or the like, which when inflated can conform to the interior surface of the hollow body structure. It will be appreciated, however, that a variety of other expandable members, such as expandable coils, expandable cages, and other conformable members could be provided in place of the balloon 14. Use of the balloon is particular convenient, and it is presently contemplated as the preferred mode for carrying out the invention.

The balloon 14 can be inflated through an annular inflation lumen 16 which is defined by an inflation tube 18 mounted coaxially about the rigid shaft 12. The inflation tube 18 may itself be rigid, e.g., a metal tube, or may be a flexible polymeric sheath formed over the shaft 12. Polymeric inflation sheaths may be rigid or flexible, although flexible sheaths will usually be non-elastic so that they will not expand substantially under the inflation pressure being applied to the inflatable balloon 14. A preferred material for the inflation tube 18 is surgical stainless steel since it enhances the rigidity of the shaft 12.

The manipulation device 10 will further include a sharp tip 20 disposed generally at the distal end of rigid shaft 12. In this particular embodiment, the sharp tip 20 is formed at the distal end of a rigid tube 22 which can be axially translated between a distally extended configuration (as illustrated in FIG. 2) where the sharp tip 20 defines the distal tip of device 10 and a retracted configuration (as illustrated in FIG. 3) where the inflation balloon 14 is exposed at the distalmost point of the device.

The manipulation device 10 further comprises a coaxial sleeve 30 formed over the tube 22 and terminating in a resilient tip element 32. The resilient tip element 32 is illustrated as a metal spring 34, typically composed of stainless steel, covered by a thin plastic or elastic membrane 36. The purpose of the resilient tip is to seal about the penetration formed by the sharp tip 20 in the wall of the body structure. The resilient tip 30 can conform to the exterior of the wall about the penetration and will compress against the force of spring 34 as the tip is urged against the wall of the body structure (after penetration). Other structures, such as bellows end accordion configurations, could also find use. The sleeve 30 itself will be generally rigid with sufficient hoop strength to withstand the negative pressure of aspiration. Various polymeric materials, such as polyethylene and polyvinyl chloride, will be suitable.

Figure 2:
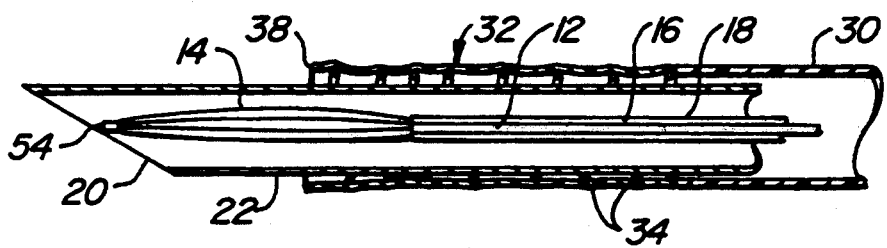
FIG. 2 is a side elevational view of the distal end of the device of FIG. 1, shown in section with a sharp tip element being advanced and a balloon element being deflated.
Figure 3:
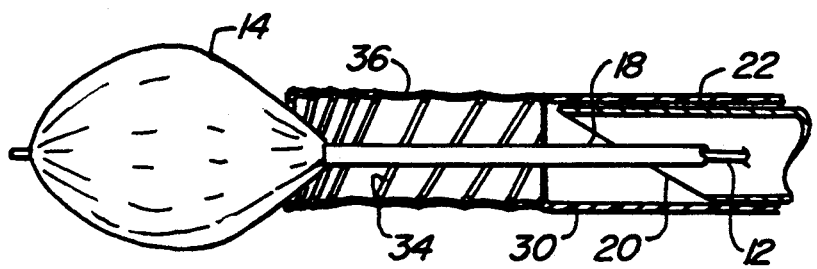
FIG. 3 is a side elevational view similar to FIG. 2, except that the sharp tip element has been retracted and the balloon element has been inflated.
Figure 4:
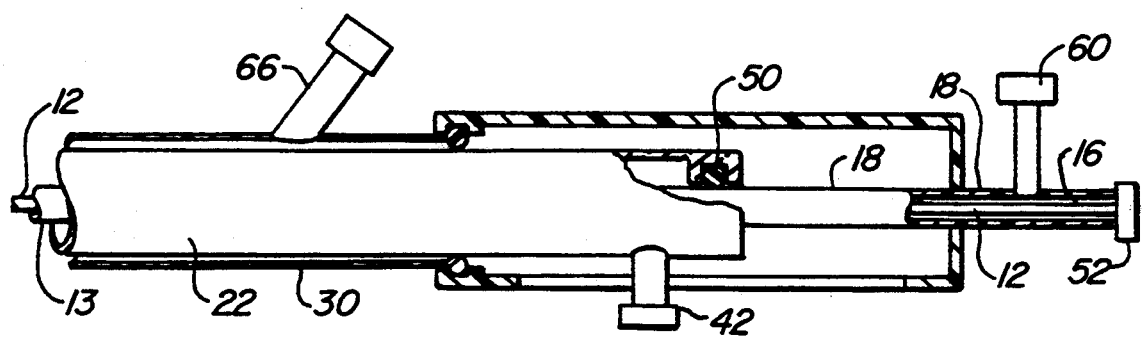
FIG. 4 illustrates the proximal end of the manipulator device of FIG. 1, shown in partial section with portions broken away.

In a preferred aspect of the present invention, the leading edge 38 of the resilient tip 32 will be located over the balloon 14, usually being located approximately half way down the length of the balloon as illustrated in FIG. 2. In this way, after the balloon is fully inserted into the desired body structure, the resilient tip will necessarily be compressed. The resulting spring force will assure that a relatively tight seal is achieved between the tip 33 and the outside wall of the body structure, further helping to minimize leakage.

A housing 40 is disposed at the proximal end of rigid shaft 12 and provides the necessary inflation and aspiration connections for the device, as well as providing means for axial translation of the sharp tip 20. Axial translation is effected by a handle 42 which is attached to the proximal end of the tube 22 which carries the sharp tip 20 at its distal end. The handle 42 travels in a slot 44 formed axially in the housing 40, including detents 46 and 48 for securing the tube 22 and tip 20 in their forwardmost and rearwardmost positions. An O-ring 50 provided at the proximal end of tube 22 to seal against the exterior of inflation tube 18. In this way, the open end of tube 22 is isolated from the outside (to inhibit gas leakage in laparoscopic procedures).

Rigid shaft 12 terminates at its proximal end in a connector 52 which may be interconnected with a suitable aspiration source (not illustrated) in order to drain the interior of the hollow body structure. The shaft 12 will typically be a hollow tube having an open distal end 54 so that the contents of the body structure can be drained by aspirating through the connector 52 after the shaft 12 has been introduced, typically prior to balloon inflation.

A second connector 60 is formed on the inflation tube 18 and communicates with the annular inflation lumen 16. In this way, balloon 14 can be inflated by applying an appropriate inflation medium, such as saline, air, or the like, through the connector 60. The inflation pressure will depend on the nature of the balloon 14 as well as the nature of the body structure being expanded. In the case of gallbladders being expanded with silicone rubber balloons, the inflation pressure will typically be in the range from about 0.5 to 5 psi, usually being in the range from about 1 to 2 psi. The total expanded volume of the balloon 14 (when used for gallbladder or manipulation) will typically be in the range from about 25 to 75 ml, usually being from 40 to 60 ml.

A third connector port 66 is provided on the coaxial sleeve 30 and is suitable for connection to an aspiration source. In this way, the region surrounding the penetration can be aspirated through the seal formed by resilient tip 32.

The overall dimensions of the device 10 will be selected depending on the hollow body structure being treated. For the treatment of the gallbladder, the device 10 will typically have a length in the range from about 30 to 75 cm, usually being from about 40 to 50 cm. The maximum diameter of the device, i.e., the outside diameter of the coaxial sleeve 30, will typically be less than 10 mm, preferably being in the range from about 5 mm to 7 mm.

Figure 5:
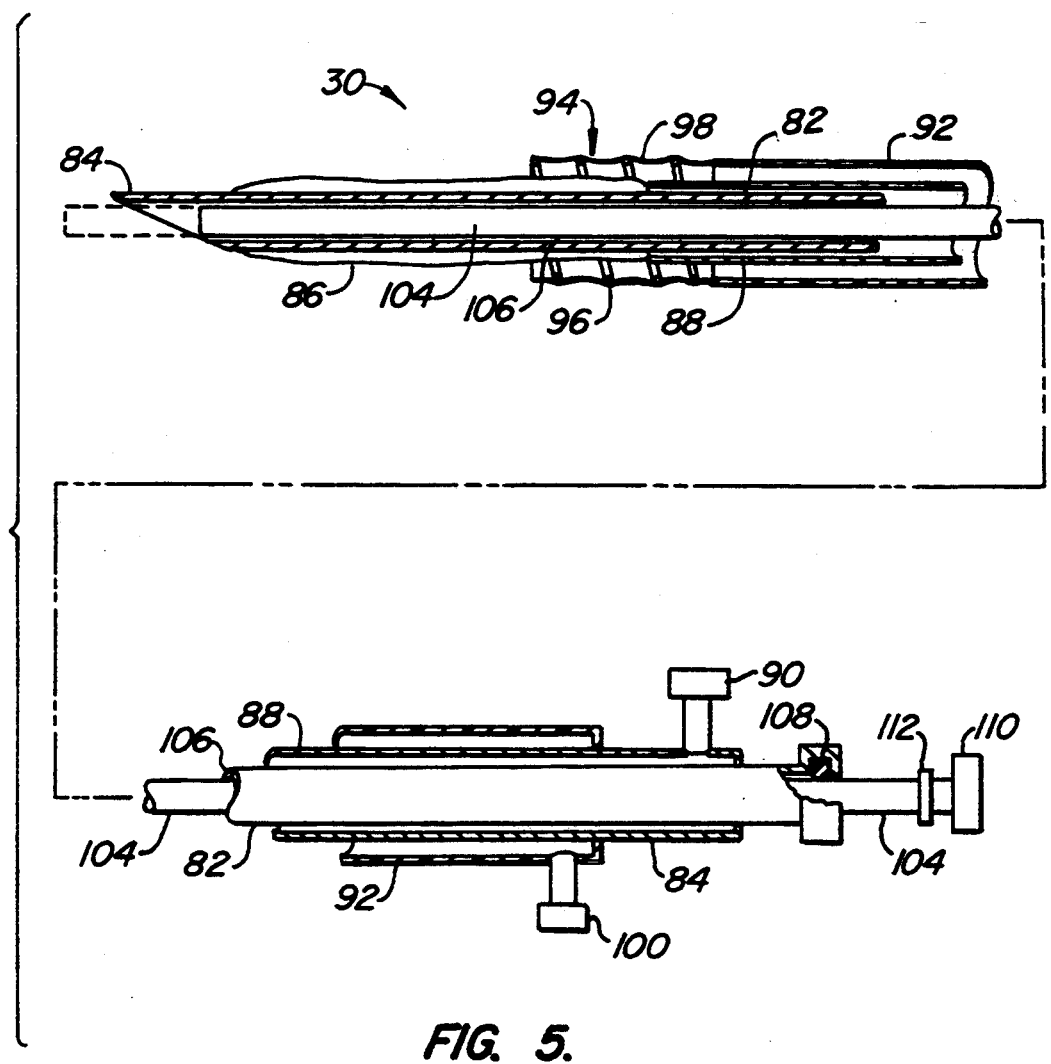
FIG. 5 illustrates an alternate embodiment of a manipulator device constructed in accordance with the principles of the present invention.

A second embodiment 80 of the manipulation device of the present invention is illustrated in FIG. 5. The device 80 comprises a rigid shaft 82 having a sharp tip 84 formed at its distal end. The rigid shaft 12 will usually be formed from metal or a rigid plastic, typically being surgical stainless steel. An inflatable balloon 86 is secured to the distal end of the rigid shaft 82 and will lie just proximally of the sharp tip 84. The balloon 86 will typically be composed or an elastic polymer, such as silicone rubber, and will be inflatable through an inflation tube 88 which is coaxially mounted over the rigid shaft 84. The inflation tube 84 is connected through a connector port 90 located at the proximal end thereof. An outer sleeve 92 is formed coaxially about the inflation tube 88 and terminates in a resilient tip 94, typically formed from a spring 96 and elastic membrane 98. The outer tube 92 is connected to an aspiration port 100 at its proximal end to permit aspiration around the penetration formed by sharp tip 84 when inserted through the wall of the body structure.

A protection rod 104 is slidably mounted in an axial lumen 106 of the rigid shift 82. An O-ring 108 provides a sliding seal between the proximal end of rigid shift and the exterior of protection rod 104 to isolate the interior of the body structure when the device 80 is in use. The protection rod 104 may be extended distally from rigid shaft 82, as illustrated in broken line, in order to protect the hollow body structure from the sharp tip 84 after the device has been inserted through the body structure wall. The protection rod 104 can be axially advanced and retracted simply by pulling on a proximal connector 110. A stop member 112 is provided to prevent over extension of the protection rod 104. Connector 110 also provides connection to a suitable aspiration source for drainage of the interior of the body structure. The protection rod 104 includes a hollow lumen which provides a drainage path through the device 80.

Figure 6:
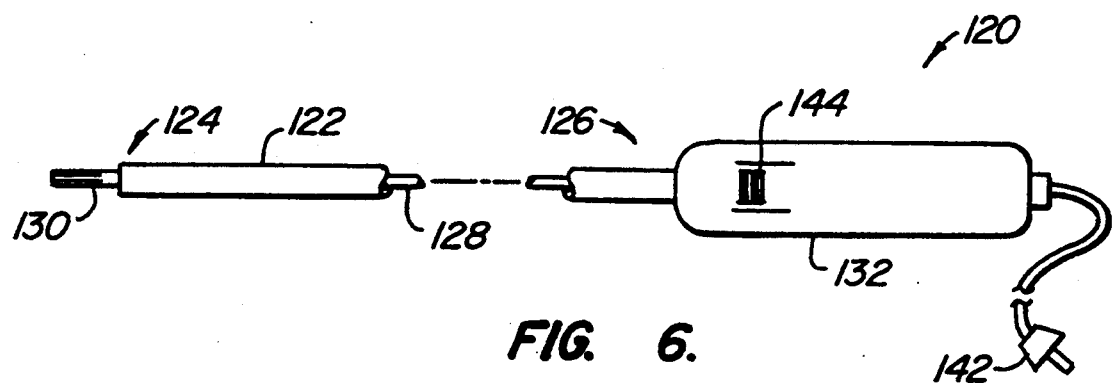
FIG. 6 is a side elevational view of a dissection device constructed in accordance with the principles of the present invention.
Figure 7:
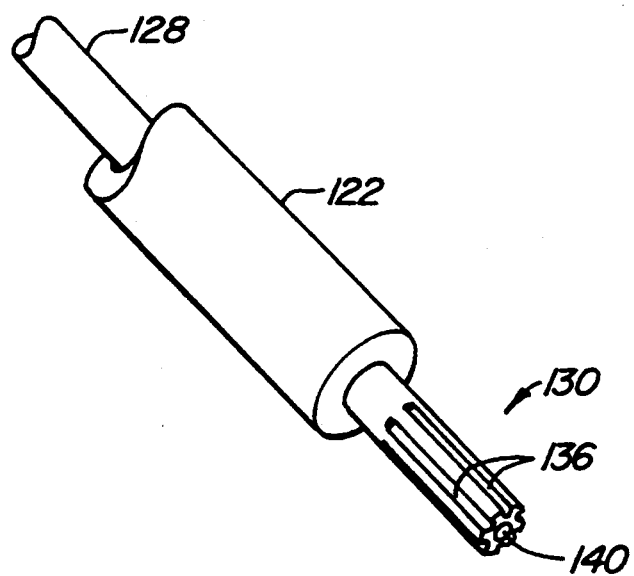
FIG. 7 is a detailed view of the distal end of the dissection device of FIG. 6, illustrating the dissection head.

Referring now to FIGS. 6 and 7, a dissection device 120 constructed in accordance with the principles of the present invention will be described. The dissection device 120 comprises s rigid shaft 122 having a distal end 124 and a proximal end 126. A drive shaft 128 extends through a central lumen of the shaft 122 and terminates in a dissection head 130 at its proximal end. A handle 132 is connected to the proximal end 126 of shaft 122 and includes a motor drive means capable of rotating or oscillating the drive shaft 128. The frequency of rotation (or oscillation) will typically be from about 2000 rpm (or Hz) to 20,000 rpm (or Hz), preferably being in the range from about 5000 rpm (or Hz) to 10,000 rpm (or Hz). A switch 144 will be provided on handle 132 for turning on and off the dissection head 130.

The dissection head 120 is formed as a cylindrical body having a plurality of axial channels 136 formed therein. The cylindrical body has a length generally in the range from about 2 mm to 20 mm, preferably being in the range from about 5 mm to 15 mm, and a diameter in the range from about 1 mm to 10 mm, preferably in the range from about 1.5 mm to 4.0 mm. Usually, from about 4 to 10 axial channels will be formed, more usually being equally circumferentially spaced-apart.

The dissection device 120 is particularly well suited for introduction through a trocar sleeve for use in laparoscopic and other minimally invasive surgical procedures. The diameter of shaft 22 will be sufficiently small to permit such introduction, typically being 5 mm or less. The dissection device 120 is used by contacting the dissection head 30 at the dissection boundary, i.e, the interface between the tissue and body structure to be dissected from the tissue, and initiating rotation and/or oscillation of the head. Use of the high frequency rotation or oscillation has been found to provide a relatively clean separation between the tissue and body structure with minimal risk of bleeding, perforation, or other undesirable injuries.

Preferably, the dissection device 20 will further include an electrode 140 at its distal tip. Electrode 140 can be connected to a conventional electrocautery power supply, typically a monopolar power supply through a connector 142 which is disposed at the proximal end of the handle 132. Thus, the dissection device 20 can be used to cauterize any cuts or tears which are accidentally caused, without need to introduce a separate electrocautery device.

Figure 8A:
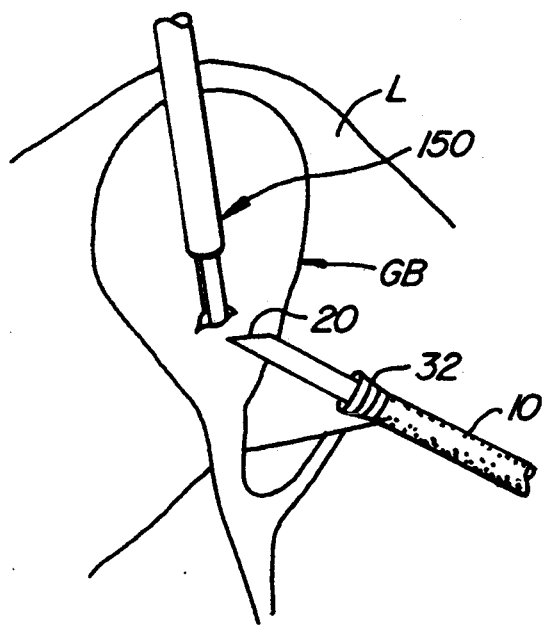
FIGS. 8A-8C illustrate the method of the present invention for manipulating and dissecting a gallbladder.
Figure 8B:
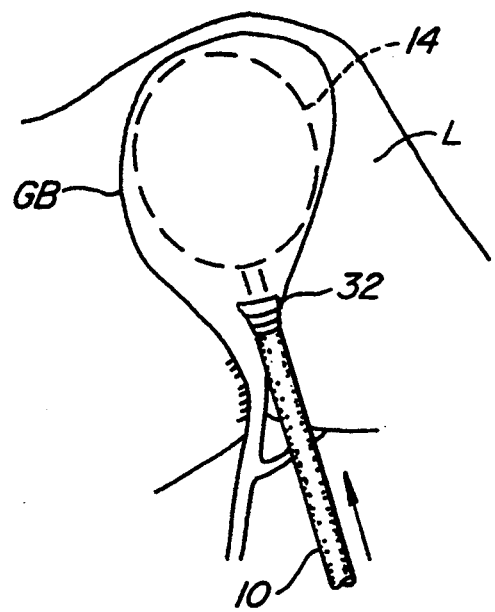
Figure 8C:
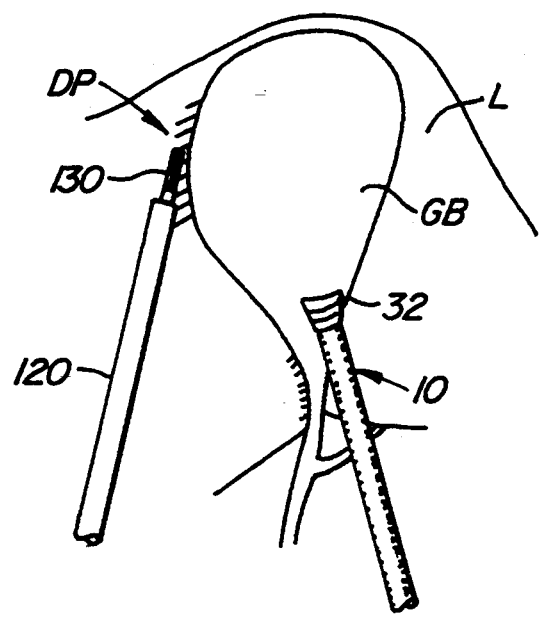

Referring now to FIGS. 8A–8C, use of the manipulation device 10 and the dissection device 120 for performing a gallbladder removal procedure (cholecystectomy) will be described. The figures illustrate the gallbladder GB being dissected from the liver L. The instruments utilized, including both the manipulation device 10 and the dissection device 120, will have been introduced through conventional trocar sheaths in a well known manner for performing laparoscopic cholecystectomy.

Initially, a portion of the outside wall of the gallbladder GB is grasped with a conventional forceps grasper 150, as illustrated in FIG. 8A. The sharp tip 20 of the manipulator device 10 is then penetrated through the wall of the gallbladder GB next to the region which is held in place by the graspers 150.

After the penetration has been achieved, device 10 is advanced forward until the resilient tip 32 forms a seal about the site of penetration, as illustrated in FIG. 8B. The sharp tip 20 will be retracted by axially translating the tube 22 in a proximal direction, and the contents of the gallbladder (bile) will be withdrawn through the interior lumen of the shaft 12. After the contents have been largely drained, the balloon 14 is inflated (as illustrated in broken line in FIG. 8B) to fill the void which has been left and expand the gallbladder GB, usually distending the gallbladder slightly to improve control and access. The device 10 may then be used to manipulate the gallbladder GB and expose the dissection plane DP, i.e. the interstitial plane between the gallbladder and the liver bed L.

The tissue dissection device 120 is next introduced, and the dissection head 130 contacted with the dissection plane DP (FIG. 8C). The dissection head 130 is actuated and used to carefully separate the exposed wall of the gallbladder GB from the liver bed L. It will be appreciated that the manipulator device 10 will be constantly repositioned to expose the dissection plane DP in an optimum manner. The dissection is continued until the gallbladder GB is completely detached from the liver bed L and other surrounding tissue. The inflated balloon 14 can then be deflated, the manipulator device 10 withdrawn, and the gallbladder removed through a trocar sleeve in a conventional manner.

Figure 9:
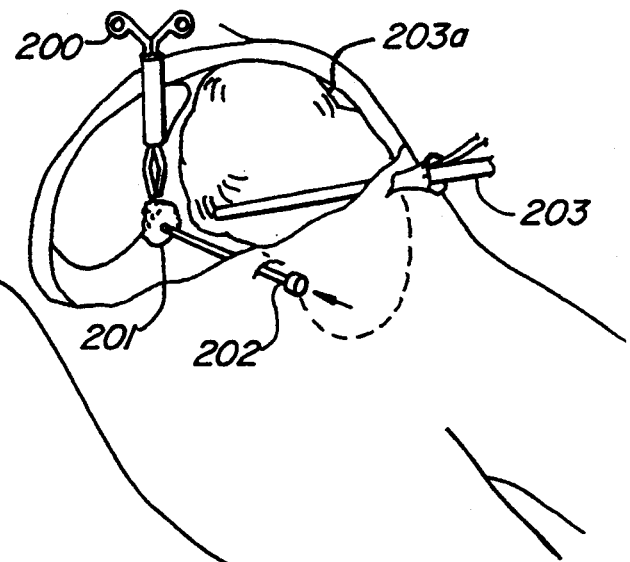
FIGS. 9, 10 and 11 illustrate the method of the invention for manipulating and dissecting the gallbladder in conjunction with an abdominal lifting device to facilitate access.
Figure 10:
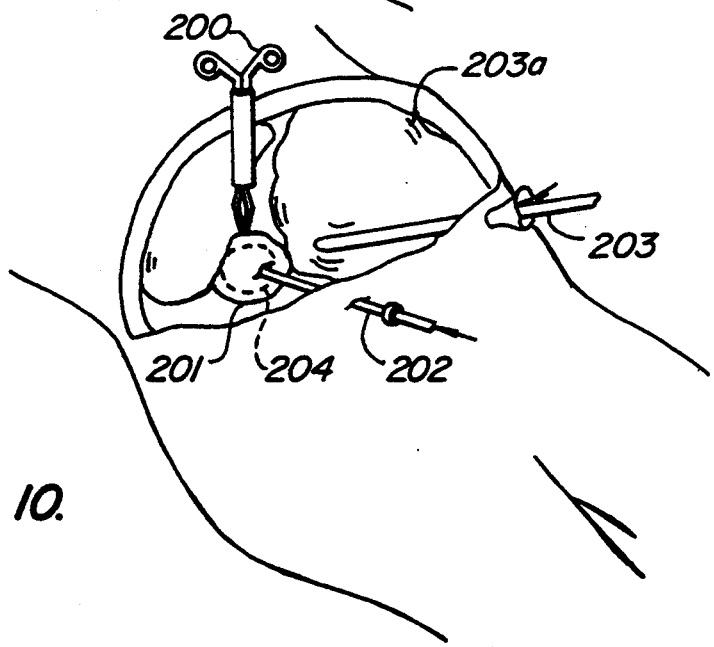
Figure 11:
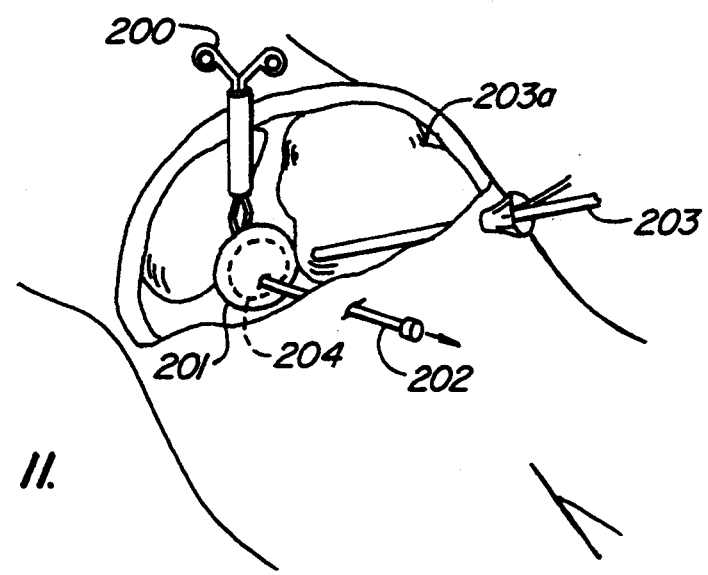

FIGS. 9, 10 and 11 are perspective views of a device according to the present invention shown in place within the abdominal cavity with a body, with parts broken away for illustration and laparoscopic forceps extended into gripping engagement with the gallbladder. These figures sequentially illustrate the steps of distention and manipulation device laparoscopically into the abdominal cavity and into a gripping engagement with the gallbladder. Referring to FIG. 9, forceps 200 are laparoscopically extended into gripping engagement with the gallbladder 201. The procedure is viewed through an endoscope 203 located within an abdominal balloon lifting device 203a. With the gallbladder so gripped, a laparoscopic distention, manipulation and removal tool 202 according to the invention, is extended into the abdominal cavity in piercing engagement with the gallbladder, as depicted by the arrow line in FIG. 10. The tool 202 takes the form of a dual lumen tubular needle having a sharpened open end through which the contents of the gallbladder may be drawn and an annular balloon which may be inflated through the lumen of the tool communicating therewith. Once the tool has been used to evacuate the contents of the gallbladder, the balloon 204 is inflated and assumes internal gripping engagement with the gallbladder. The tool may then be manipulated, thus maneuvering the gallbladder within the abdominal cavity or exerting tension on it as depicted by the arrow line in FIG. 11. Depending upon the size of the gallbladder, the removal of the organ may require some enlargement of the incision through which the tool extends. The forceps would be released from the gallbladder to permit its manipulation using only the balloon tool. The entire procedure is viewed through the endoscope 203. Following deflation and removal of the balloon, the gallbladder is seized by forceps for further manipulation.

Figure 12:
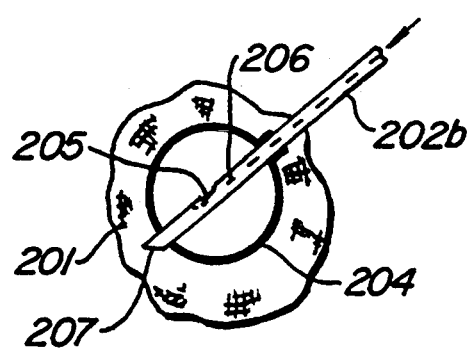
FIGS. 12 and 13 illustrate two embodiments of the manipulating device of the invention.
Figure 13:
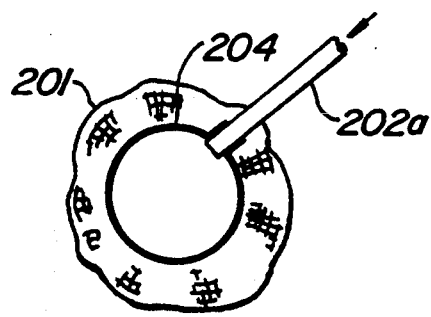

FIGS. 12 and 13 show detail of the tool 202. The device of FIG. 13 corresponds to that of FIG. 12 except that the tubular needle 202a has a single lumen only for inflation of the balloon 204 and that the needle 202a does not extend fully through the balloon. Thus, the embodiment in FIG. 13 cannot be used to evacuate the gallbladder. In FIG. 12, the needle 202b accommodates a separate channel 206, communicating with the interior of balloon 204 through orifice 205. The end of the needle 202b accommodates orifice 207 through which the contents of gallbladder 201 may be evacuated.

Figure 14:
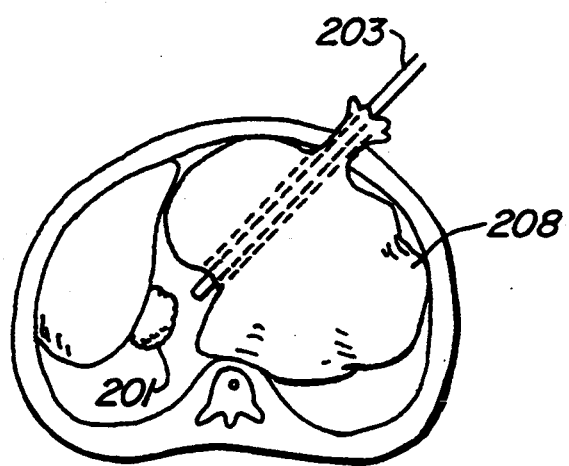
FIG. 14 illustrates a modification of the method illustrated in FIGS. 9-11 wherein the gallbladder is viewed from the exterior of the abdominal lifting device.

FIG. 14 is a cross-sectional view similar to the above, showing a modified version of the invention wherein the endoscope 203 extends fully through a balloon 208 which serves as an abdominal lifting device. The gallbladder 201 is then viewed directly, rather than through the balloon 208.

Figure 15:
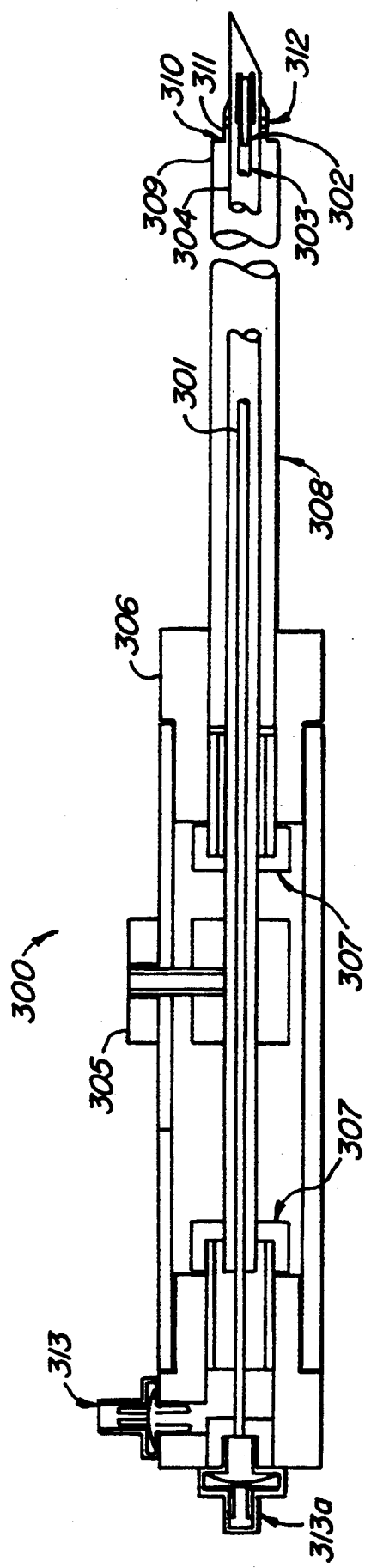

Referring to FIG. 15 there is shown an embodiment of the tool according to the invention for insertion into the gallbladder for draining the contents thereof and inflating a balloon for manipulation. This embodiment permits removal of all rigid or semi-rigid structures from within the gallbladder (or other organ) prior to manipulation to avoid the risk of organ injury. The further improvement is provided in that the needle tip used for organ entry is retracted out of the organ to prevent injury. Referring to FIG. 15, the organ manipulator device 300 is a rigid structure which allows for control of the displacement of the attached organ. Therefore, the manipulator device may be of a metallic construction or of other suitable rigid material, whereby the rigidity is imparted by one or more of the three concentric tubular members which comprise the device. The innermost tubular member 301 holds an elastomeric member 302, which will be inflated inside the organ to hold and distend the organ for manipulation. An elastomeric balloon is preferred because of its initial small profile upon entry into the organ and its expansion capacity upon inflation to fill the inside of the organ. The elastomeric member 302 is shown in an inverted position within the innermost tube 301. The elastomeric member 302 is everted into the organ after protrusion of a small length of the distal end 303 of the innermost tube 301 into the organ. This is an improvement in that it minimizes the length of the innermost tube which must be placed into the organ prior to inflation. The end of the elastomeric member 302 is bonded to the distal end 303 of the innermost tube 301 in a suitable manner, for example by use of adhesive, adhesive with an outer plastic shrink wrapping, adhesive with an outer suture winding, and the like. The innermost tube 301 may be made of a rigid plastic material such as nylon, PVC, polyethylene, and the like, or, most preferably, stainless steel.

The innermost tube 301 is concentrically disposed within a tubular needle 304 having a sharp point for piercing the organ. The needle 304 may extend to completely enclose the innermost tube 301, in the closed configuration of the device 300, and then may be mechanically retracted proximal to the distal end 303 of the innermost tube 301 to expose the inner most tube to the interior of the organ. Preferably, the needle 304 is made of stainless steel. Retraction of needle 304 is accomplished by exterior handle 305 affixed to needle 304 within the housing 306 at the proximal end of the device 300. Seals 307 are provided to allow for movement of the tubular needle 304 in a gas tight manner. The outermost tube 308 is concentric with tubular needle 304 and is fixed in position with respect to the innermost tube 301, with the distal end 309 of the outer most tube 308 being approximately flush with the distal end 303 of the innermost tube 301. The outermost tube 308 is stepped down to form a step 310 at its distal end, with the inner diameter at the step providing a slip fit with the outer diameter of the tubular needle 304. The length of the step is preferably about 0.1 to 0.15 inches. The advantage of the step 310 is to provide a mechanical stop during insertion of the device 300 into the organ. When the needle tip of the tubular needle 304 is extended and used to puncture an organ, the needle tip and the stepped down portion 311 of the outer tube 308 easily enter the organ wall. When the outer wall of the organ impacts the step 310 on the outer tube 308, the forward progress of the organ manipulator device 300 is halted, thereby guarding against excessive needle travel and puncture of the back wall of the organ. The stepped down portion 311 may contain radial holes 312 or slots placed around its circumference to assist in drainage of the organ contents when the needle tip is retracted. Vacuum suction may be applied in the volume between the outer tube 308 and the needle 304 as well as in the volume between the needle 304 and innermost tube 301 by application of a vacuum at aspiration port 313 which is in communication with the volume between the innermost tube 301 and tubular needle 304. Upon retraction of the needle 304 into the outer most tube 308, aspiration will also be effective within the volume at the distal ends between the needle 304 and the outermost tube 308. The outermost tube 308 is also preferably made of a rigid material such as plastic, (nylon, PVC, polyethylene and the like) or stainless steel. The housing 306 at the proximal end of the device 300 accommodates the port 313a and the fittings for inflation of the elastomeric member 302 through the interior of the innermost tube 301. The tubular needle 304 may be locked in its forward (extended) position for entry into the organ by a suitable locking mechanism (not shown) and unlocked and retracted prior to the balloon inflation. The tubular members 301, 304 and 308 are sealed on their interior volumes such that no gas leaks occur when the device is introduce into the abdomen or organ for laparoscopic surgery. Inflation of the elastomeric member 302 may be accomplished using a separate inflation device such as a syringe or a pump. A pump may be built directly into the housing 306.

Figure 16:
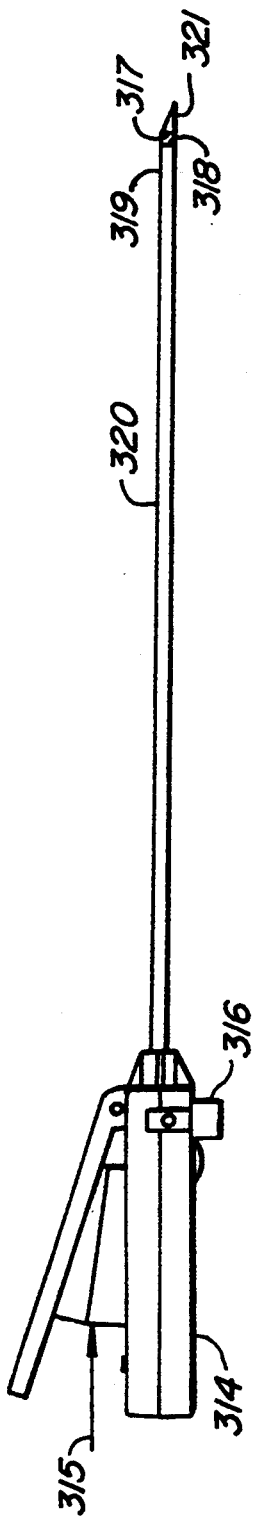

Referring to FIG. 16 there is shown an alternative embodiment of the device of FIG. 15 wherein a pump is built into the housing 314. Pumping is actuated by a bellows 315 and withdrawal of contents of the interior of the organ is conducted through aspiration port 316. There are shown the step 317 and radial holes 318 at the distal end 319 of the outermost tube 320. Only the tip of the tubular needle 321 is shown.

Referring to FIGS. 17A, B and C there is shown the device of FIGS. 15 or 16 in use. For convenience, the same numerals on corresponding elements as described in FIG. 15 will be used in connection with the description of FIG. 17. Referring to FIG. 17A, the distal end 309 of the outermost tube 308 is advanced into an abdominal cavity (not shown) through a properly sized trocar with the needle 304 retracted into the tube 308 to protect the needle tip. The trocar seals against the tube 308 to maintain the pneumoperitoneum. The needle 304 is advanced out of the outer tube 308 (FIG. 17B) and a grasping instrument (not shown) stabilizes the wall of the organ 400 as the extended needle punctures through the wall and stops at the end of the outer tube step 310. The needle is then unlocked from its extended position and retracted (dotted outline in FIG. 17B) then suction is applied through the aspirator port (not shown) which drains the fluid contents from the organ. Then air is pumped through the innermost tube 301 (FIG. 17C) to evert the balloon 302 out of the inner most tube into the organ and pumping is continued to inflate the balloon within the organ. The organ may now be manipulated for dissection and isolation for removal. Following organ dissection, the balloon is deflated to allow detachment of the organ.

Figure 18:
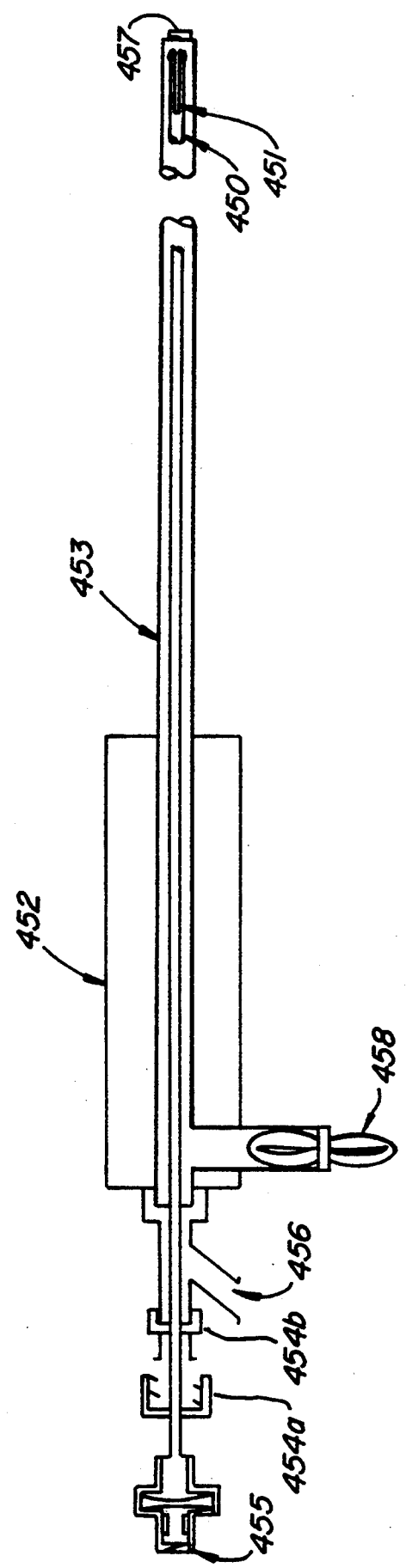
Figure 18A:
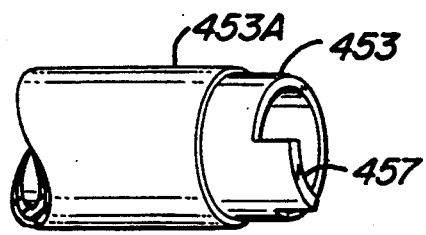

Referring to FIGS. 18 and 18A, another embodiment of the device is shown having two concentric tubes instead of three, whereby electrocautery is used to enter the organ instead of a needle. The inner tube 450 holds an inverted elastomer balloon 451 and tube 450 is connected to a slide arrangement within the handle 452 which allows for extension and retraction with respect to the outer tube 453. The mechanism in the handle 452 provides a locking mechanism 454A and B to lock the inner tube 450 in an extended position. The proximal end of the inner tube 450 accommodates inflation port 455 for inflating the balloon 451. A drainage port 456 is provided for evacuating the contents of the organ by aspiration. The inner tube 450 is preferably made of a rigid material such as stainless steel with an outer insulative sleeve which is electrically insulated with a material such as polyvinyl chloride, polyethylene nylon or other plastic. The outer tube 453 is also preferably stainless steel but may be made of another electrically conducting material and provides a loose fit with the inner tube 450. The outer tube 453 is electrically insulated on the outside with insulation 453A, leaving a small portion of the distal end (preferably 2 to 3 millimeters of length) uninsulated at the tip. Referring to the detail of the tip in FIG. 18A, the exposed distal tip 457 is cut away, preferably so that only an arc of less than about 180 degrees of the circumference of the outer tube 453 remains. This allows for cutting of a small curve slit by cauterization in the organ wall instead of a full circle, aiding in the sealing of the organ wall against the shaft of the device and minimizing the amount of heat-necrosed tissue that may cause the entry hole to enlarge upon traction and manipulation of the device. An electrocautery connector 458 is provided in the handle 452 to allow hookup to an electrocautery generator (not shown). In use, the inner tube 450 is initially withdrawn (preferably approximately 1-2 cm.) into the outer tube 453 during entrance through the wall of the organ by cauterization. This prevents the inner tube 450 and balloon 451 from being heated by the tip of the outer tube during cautery use. Following entrance of the outer tube into the organ, suction aspiration of the organ contents is performed through port 456. The inner tube 450 is then advanced forward and locked in an extended position. Air is pumped through port 455 to evert and inflate the balloon 451 in preparation for the organ manipulation.

Referring to FIG. 19, another embodiment of the organ balloon manipulator is shown. A needle 500 is provided within a rigid inner tube 501 and a concentric rigid outer tube 502. An elastomeric sleeve 503 is attached having one edge attached to the distal ends of the inner and outer tubes, respectively. A seal 504 is provided at the proximal end of the device to allow the inner tube 501 to translate longitudinally with respect to the outer tube 502 while maintaining a gas tight seal. A locking mechanism 505A and B allows the needle 500 to be positioned and locked with respect to inner tube 501, so that the needle 500 is in an armed configuration. An inflation port is provided for 506 to provide for inflation of the elastomeric sleeve 503 and an aspiration port 507 is provided for evacuation of the organ contents. In use, the needle 500 is locked in a forward position and the device is advanced to puncture through the organ wall 510 (FIGS. 19A and B). The needle 500 is unlocked and withdrawn at least partially into the inner tube 501 to prevent injury to the organ. Advancement of the device is continued until the outer tube 502, lies within the cavity of the organ. The elastomeric sleeve balloon 503 is inflated (FIG. 19B) and inner tube 501 is retracted with respect to the outer tube 502 until the tips of the inner and outer tubes meet. This action causes the balloon 503 to take on a toroidal shape and removes all rigid tubes from inside the organ.

Although the foregoing invention has been described in detail for purposes of clarity of understanding, it will be obvious that certain modifications may be practiced within the scope of the appended claims.

What is claimed is:

1. A method of removing the gallbladder from an abdominal cavity, said method comprising laparoscopically inserting a compression elastic balloon into the abdominal cavity and inflating said balloon to displace the liver and gallbladder for access, wherein the gallbladder is gripped and laparoscopically withdrawn by:
   a) externally gripping the gallbladder;
   b) laparoscopically piercing the gallbladder with a needle carrying a gripping balloon to dispose the gripping balloon within the gallbladder;
   c) inflating the gripping balloon to internally grip the gallbladder;
   d) manipulating the needle with the gallbladder engaged; and,
   e) withdrawing the needle with the gallbladder engaged therefrom the body.

2. A method according to claim 1, wherein the gallbladder is drained through the needle prior to inflation of the gripping balloon.

3. A device for manipulating a hollow body structure, said device comprising a first rigid tubular member having a proximal end and a distal end;
   a second rigid tubular member internal to said first tubular member;
   an expandable member affixed at the distal end of said second tubular member, said expandable member being inverted within said second tubular member;
   a third tubular member, accommodating piercing means on the distal end thereof, said third tubular member being slidable within said first tubular member to expose said piercing means beyond the distal end of said first tubular member, and slidable to retract said piercing means into said first tubular member; and
   means for selectively expanding said expandable member from an unexpanded configuration to an expanded configuration; and means for aspiration of fluid from near the distal end of said device to the proximal end of said device.

4. A device according to claim 3 further comprising a reduction of diameter of said first tubular member at the distal end thereof to form a tip and a surface which serves as a stop when said tip is moved axially to penetrate an opening of a size smaller than the outer diameter of said first tubular member.

5. A device according to claim 4 wherein said tip defines a primary axial opening for accommodating said third tubular member and further defines at least one orifice communicating with said axial opening.

6. A device according to claim 3 further comprising gripping means at the proximal end thereof, said gripping means communicating with said third tubular member to axially advance said piercing means to an extended position protruding from the distal end of said first tubular member.

7. A device according to claim 6 further comprising locking means to lock said piercing means in an extended position.

8. A device according to claim 7 further comprising a seal at the proximal end of said third tubular member slidably contacting said second tubular member.

9. A device according to claim 7 wherein said locking means is disengageable to disengage said piercing means from the locked extended position to retract said third tubular member to a retracted position within said first tubular member.

10. A device according to claim 3 further comprising pumping means for introducing gas or air through said second tubular member to inflate said expandable member.

11. A device according to claim 10 wherein said pumping means provides gas or air to evert said expandable member out of said second tubular member.

12. A device according to claim 10 wherein said pumping means comprises bellows.

13. A device according to claim 10 wherein said pumping means is a piston.

14. A device according to claim 3 further comprising means for releasing pressure to deflate said expandable member.

15. A device according to claim 3 wherein said piercing means comprising a cauterizing tip on said rigid shaft.

16. A device according to claim 15 wherein said rigid shaft is electrically insulated.

17. A device according to claim 15 wherein said cauterizing tip comprises a tab extending from the distal end of said shaft, said tab capable of cauterizing an arc in tissue of approximately the radius of said first tubular member with a length of less than about one-half of the diameter thereof.

18. A device for manipulating a hollow body structure, said device comprising a first rigid tubular member having a proximal end and a distal end; a second rigid tubular member located within said first tubular member and slidable within said first tubular member; an expandable elastomer sleeve having one edge circumferentially attached to the distal end of said first tubular member and the other edge circumferentially attached to the distal end of said second tubular member; piercing means within said second tubular member, said piercing means comprising a hollow rigid shaft with a pointed tip at the distal end thereof, said shaft comprising means for aspirating fluid from near the distal end of said device to the proximal end of said device; means for selectively expanding said expandable elastomer sleeve from an unexpanded configuration to an expanded configuration.

19. A device according to claim 18 wherein the distal end of said second tubular member is extendable beyond the distal end of said first tubular member to maintain a flat shape to said expandable elastomer sleeve.

20. A device according to claim 18 further comprising a slidable seal at the proximal end of said device for longitudinal translation of said second tubular member within said first tubular member while maintaining a gas tight seal therebetween.

21. A device according to claim 18 wherein said hollow shaft is lockable in place by a locking means at the proximal end of said device in a position wherein said pointed tip extends beyond the distal end of said first and second tubular members.

22. A device according to claim 21 wherein said hollow shaft is unlockable for withdrawal of said pointed tip into said first or second tubular members.

23. A device according to claim 18 wherein said second tubular member is slidable for withdrawal of the distal end thereof into the distal end of said first tubular member, thereby forming an expandable annulus from said expandable elastomeric sleeve.

24. A method of manipulating a hollow body organ comprising the steps of:
piercing said organ to form an opening with a device comprising an elongate shaft, a retractable piercing means protruding from one end of said shaft and an inverted expandable member having a peripherally sealed mouth located within said shaft;
said shaft having a reduction in diameter to define a tip at said end and stopping means for impeding entry of said shaft into said body organ when said tip is moved longitudinally through said opening;
inserting said piercing means and said tip into said body organ until insertion is impeded by said stopping means;
retracting said piercing means into said shaft;
everting said expandable member into said organ by forcing air into said mouth of said member;
inflating said expandable member within said organ; and
manipulating said organ with said device.

25. A method according to claim 24 further comprising the step of withdrawing fluid contents from said organ through said device prior to inflating said expandable member.

26. A method according to claim 24 wherein said stopping means comprises an annular surface.

27. A method for manipulating a hollow body organ comprising the steps of piercing said organ by electrocautery with an electrocauterizing tip on a device comprising an elongate shaft having said tip at one end of said shaft and an expandable member having a peripherally sealed mouth located within said shaft, wherein said tip comprises an arcuate tab extending from said end of said shaft;
inserting said end of said shaft into said organ through the orifice in said organ formed by said tip;
inflating said expandable member within said organ; and
manipulating said organ with said device.

28. A method according to claim 27 further comprising the step of withdrawing fluid contents from said organ through said device prior to inflating said expandable member.

29. A method according to claim 27 wherein said expandable member within said shaft is inverted, whereby, upon initiation of said step of inflating said expandable member, said member everts into said organ.

30. A method of manipulating a hollow body organ comprising the steps of:
piercing said organ with a device comprising telescoping interior and exterior rigid shafts in an extended position whereby the open end of said interior shaft is at one end of said device, a retractable piercing means protruding from said end of said device, and an expandable elastomeric sleeve having one edge circumferentially attached to said open end of said interior shaft and having the other end circumferentially attached to an end of said exterior shaft;
retracting said piercing means into said device;
inserting said device into said organ to the extent that said end of said exterior shaft enters said organ;
retracting said interior shaft into said exterior shaft whereby said sleeve forms an expandable annulus; and
inflating said annulus within said organ.

31. A method according to claim 30 further comprising the step of withdrawing fluid contents from said organ through said device prior to inflating said annulus.

* * * * *